United States Patent [19]
Clayberger et al.

[11] Patent Number: 5,935,797
[45] Date of Patent: Aug. 10, 1999

[54] INTERACTION OF MHC CLASS II PROTEINS WITH MEMBERS OF THE PCNA FAMILY OF PROTEINS

[75] Inventors: Carol Clayberger; Alan M. Krensky, both of Stanford, Calif.

[73] Assignee: Stanford University, Stanford, Calif.

[21] Appl. No.: 08/829,132

[22] Filed: Mar. 28, 1997

Related U.S. Application Data

[63] Continuation-in-part of application No. 08/741,530, Oct. 31, 1996, which is a continuation of application No. 08/260,548, Jun. 16, 1994, abandoned.

[51] Int. Cl.$^6$ .................................................. G01N 33/53
[52] U.S. Cl. ........................... 435/7.1; 436/501; 530/300; 530/350; 530/395; 435/7.23; 435/7.24
[58] Field of Search ..................................... 435/7.1, 7.23, 435/7.24; 436/501; 530/300, 350, 395

[56] References Cited

U.S. PATENT DOCUMENTS

| | | |
|---|---|---|
| 4,478,823 | 10/1984 | Sanderson et al. . |
| 5,130,295 | 7/1992 | Sharma et al. . |

FOREIGN PATENT DOCUMENTS

| | | |
|---|---|---|
| WO 94/04171 | 3/1994 | WIPO . |
| WO 94/20127 | 9/1994 | WIPO . |
| WO 96/35715 | 5/1996 | WIPO . |

OTHER PUBLICATIONS

Chicz, R. et al., *International Immunol.* (1994) 6:1639–1649.
Chicz, R. et al., *Nature* (1992) 358:764–768.
Chicz, R. et al., *Immunol. Today* (1994) 15:155–160.
Davenport, M. et al., *Proc. Natl. Acad. Sci. USA* (1995) 92:6567–6571.
Gorga, J.C., *Criticals Review in Immun.* (1992) 11(5):305–335.
Jardetzky, T. et al., *Proc. Natl. Acad. Sci. USA* (1996) 93:734–738.
Kuriyan et al., *J. Mol. Biol.* (1993) 234:915–925.
Liu, Z. et al., *J. Immunol.* (1992) 148:35–40.
Murphy, B. et al., *Nephrology and Hypertension* (1996) 5:262–268.
Nag, B. et al., *Proc. Natl. Acad. Sci. USA* (1993) 90:1604–1608.
Robins et al., *J. Biological Chemistry* (1994) 269:28535–28538.
Sablinski, T. et al., *Transplantation* (1992) 53:219–221.
Waga et al., *Nature* (1994) 369:574–578.
Waga et al., *J. Biological Chemistry* (1994) 269:10923–10934.
Wucherpfenning, K. et al., *J. Exp. Med.* (1995) 181:1597–1601.

*Primary Examiner*—Thomas M. Cunningham
*Attorney, Agent, or Firm*—Morrison & Foerster, LLP

[57] ABSTRACT

Present invention based on the identification of the molecular interaction that forms the basis of the immunosuppressive activity of peptides comprising residues 71–80 of an MHC Class II protein (Class II peptides). Specifically the present invention discloses that Class II peptides bind to members of the PCNA family of proteins. Based on this observation, present invention provides methods for identifying agents that can be used to modulate immune system activity.

10 Claims, 3 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 15 amino acids
      (B) TYPE: amino acid
      (C) STRANDEDNESS: single
      (D) TOPOLOGY: linear (xi) SEQUENCE DESCRIPTION: SEQ ID NO:1:

Asn Ile Ala Val Leu Lys His Asn Leu Asn Ile Val Ile Lys Arg

INTERACTION OF MHC CLASS II PROTEINS WITH MEMBERS OF THE PCNA FAMILY OF PROTEINS

RELATION TO OTHER APPLICATION

The present application is a continuation-in-part of U.S. Ser. No. 08/741,530, filed Oct. 31, 1996, which is a continuation of U.S. Ser. No. 08/260,548, filed Jun. 16, 1994, now abandoned.

This invention was made with Government support under Contract No. AI35125 awarded by the National Institutes of Health. The Government has certain rights in this invention.

TECHNICAL FIELD

The field of this invention is the modification of immune system activity.

BACKGROUND

The immune system is the subject of ever increasing scientific scrutiny. Despite the enormous interest in the immune system and the continuously expanding number of investigators, both academic and industrial, a complete understanding of the system continues to remain elusive. One of the major breakthroughs was identification of the interaction between the T-cell receptor and a major histocompatibility complex antigen. The identification that both class I and class II major histocompatibility complex antigens have a cleft which binds a small peptide provided a significant key to understanding T-cell specificity and T-cell restriction.

Despite an increase understanding of the immune system in advance of immunosuppressive therapy, the major barrier to successful transplant engraftment is the allogenic immune response that results in graft rejection or graft versus host disease. Currently available nonspecific immunosuppressive therapies are accompanied by increased risks of infection and a variety of deleterious side affects, including nephrotoxicity, hypertension, hyperlipidemia and bone disease. Even with the current armament of immunosuppressive agents, acute graft rejection and failure to achieve long-lasting graft survival persists.

Besides transplants, there are a number of other indications where suppression of T-cell proliferation and/or activation would provide a therapeutic methodology for treatment. These include autoimmune disorders, cancer, and the like. Therefore, it would be of substantial value to provide methods for identifying agents that can be used in suppressing the proliferation and/or activation of T-cells.

The present invention expands on the identification that peptides comprising at least eight amino acids from residue 65-79 of the α chain of and MHC Class II antigen (hereinafter the Class II peptides) can be used to block T-cell proliferation, CTL proliferation, differentiation and lysis. Although the activity of such peptides had been shown, the mechanism of action remained unknown.

The present invention identifies the target of the immunosuppressive Class II peptides. Based on this observation, the present invention provides an assay method and target for identifying and developing agents that can be used to block T-cell proliferation and activation, CTL proliferation, differentiation, activation and/or lysis.

In the examples below, it is shown that a peptide comprising residues 65-79 of an MHC Class II protein (Class II peptides) interacts with members of the Proliferating Cell Nuclear Antigen family of proteins (the PCNA proteins). PCNA proteins had previously been shown to be involved in both DNA replication and nucleotide excision repair (Kuriyan et al. *J Mol. Bio* 234:915–925 (1993)). PCNA had been described as a structural specific endonuclease with five prime to three prime exonuclease activity that shows homology with putative nucleotide excision repair factors including xeroderma pigmontosum complementation G protein group, *S. pombe* rad 2 and rad 13, and *S. cerevisiae* RAD 27/YKL510 and RAD 2 (for example, see Robins, et al. *J Biological Chemistry* 269:28535–28538 (1994), Waga, et al *J. Biological Chemistry* 269:10923–10934 (1994) and PCT Application WO96/35715.)

In WO96/35715, it was disclosed that PCNA interacts with Fen[1] and p21. The interaction of PCNA I with FEN[1] and/or p21 had been implicated in being responsible for initiating PCNA activity. The '715 application further showed that a fragment of the Fen[1] protein, containing the sequence motif QGRLDxFF, bound to PCNA somewhere within the center loop of PCNA and blocked PCNA/p21 interaction. (For example also see Waga, et al. *Nature* 369:574–578 (1994)). The interaction of Fen[1] or p21 with the central loop site on PCNA had been described within the art as being important in PCNA function (for example, see PCT Application WO96/35715).

Quite unexpectedly, the present invention is based on the identification that a Class II peptide, that interacts with and binds to a different portion of PCNA, effects the activity of the immune system, a function previously not ascribed to PCNA. As described below, a peptide fragment corresponding to residue 65 through 79 of a MHC Class II protein was shown to bind to the carboxyl (beta sheet) end of PCNA. This binding mediates the CTL inhibitory activity demonstrated for the MHC Class II peptides (for example see U.S. Ser. No. 08/741,530).

SUMMARY OF THE INVENTION

Figure 1:
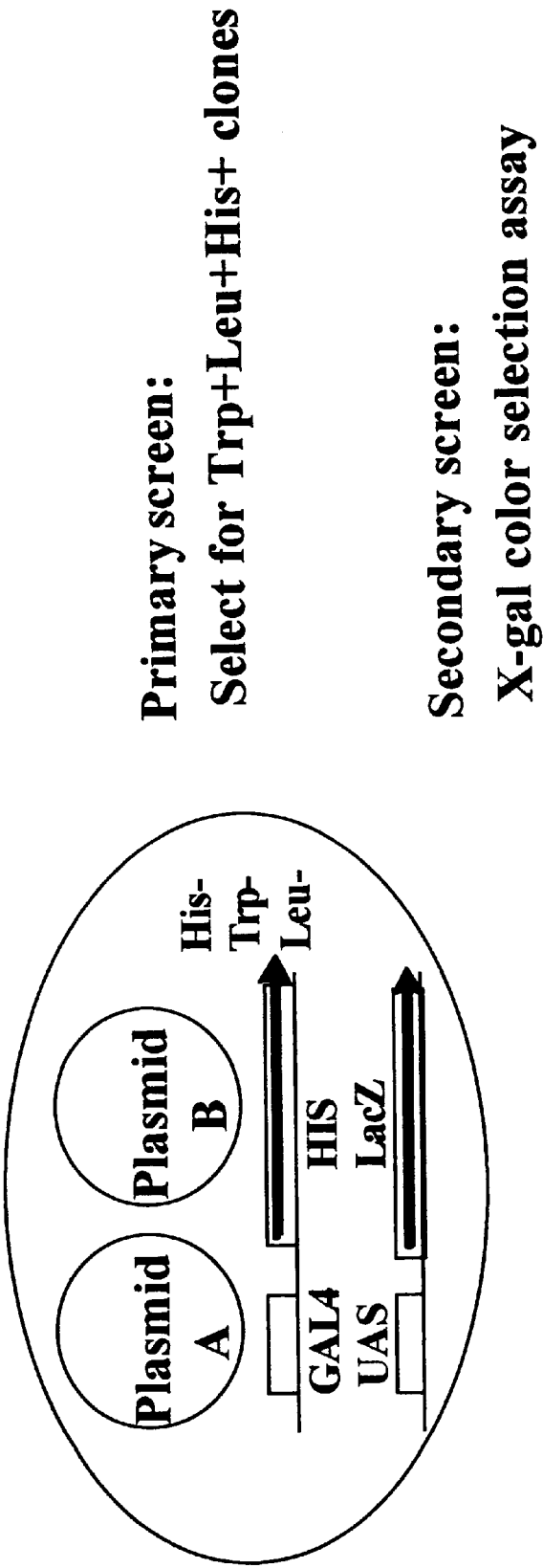
FIG. 1: Yeast two-hybrid screen for protein ligands of DQ65-79. DQ65-79 peptide was fused to GAL4 DNA binding domain (GAL4 DB) as the bait plasmid, while human cDNA was fused to the GAL4 activation domain (GAL4 AD). Both yeast His marker and LacZ reporter are under the GAL4 UAS (upstream activating sequence) control. Positive two-hybrid interaction would turn on both His and LacZ reporter gene activity.

The present invention is based, in part, on the identification of one of the mechanism by which immune responses, particularly those involving cytotoxic T-cells (CTL's), are potentiated. In the following Examples, data are provided showing that members of the Proliferating Cell Nuclear Antigen (PCNA) family of proteins interact with peptides corresponding to residues 65–79 of members of the MHC Class II proteins (hereinafter the Class II peptides) to inhibit the activity of cytotoxic T-cells (CTLs).

The present invention is further based on identifing how fragments of MHC Class II proteins, particularly residues 65–79 of the DQ 03011 allele, interact with a member of the PCNA family of proteins to modulate an immune response. In the parent application, results were presented that demonstrated that a Class II peptide could block immune responses mediated by lymphocytes, particularly T-cell differentiation, proliferation and CTL mediated lysis. In the present Examples, the ability of Class II peptides to block these immune functions was shown to be mediated by the interaction of the Class II peptide with a member of the PCNA family of proteins. This observation is important because the target of Class II proteins was previously unknown in the art and PCNA was not an obvious target of action. The identified Class II protein/PCNA interaction of the present invention can be used as a basis for making and identifying agents that can modulate immune responses. Competitive assays using PCNA and a Class II protein, in a variety of forms, can be used to identify compounds that block the same interactions as that blocked by a Class II peptide. Additionally, peptide and protein modeling techniques can be used to study the specific interactions of the Class II peptide with PCNA to rationally design or rationally select agents for testing. Such agents can be used as a therapeutic agent to inhibit immune responses in a fashion similar to that know for the Class II peptides.

DETAILED DESCRIPTION OF THE PREFERRED EMBODIMENT

A. Interaction of an MHC Class II peptide fragment with PCNA

In the Examples, data are presented that demonstrates that the immunosuppressive activity of residues 65–79 of an MHC Class II peptide is potentiated, in part, by the interaction of the Class II peptide with a member of the PCNA family of proteins. Upon interaction, immune responses, such as T-cell proliferation, differention and CTL mediated killing, are repressed. Based on these observations, one aspect of the present invention provides the specific interaction that mediates the immunorepressive activity of the Class II peptides as a basis of immunomodulatory agent identification and/or design.

As described below, this interaction can be used: 1) to identify and isolate new immunomodulating agents, 2) in methods to identify agents that can block the association of the Class II peptide with PCNA, and 3) as a target to rationally design immunomodulating agents B. Methods to identify agents that modulate immune activity The present invention provides methods for identifying agents that can be used to modulate immune activity by mimicking the the activity of Class II peptides. As shown in the Examples, the immunomodulating activity of a peptide comprising residue 65–79 of an MHC Class II protein is based on the ability of the Class II peptide to bind to a member of the PCNA family of proteins. Knowledge of this interaction provides a basis for identifying new immunomodulating agents. An agent can be selected to mimic the activity of a Class II peptide by selecting an agent that can bind to PCNA, reduce or block Class II peptide/PCNA interactions and reduce or block T-cell differentiation, proliferation and/or CTL mediated killing. Such agents can be selected as having an equivalent activity as a Class II peptide, as having a more selective activity than a Class II peptide, or as having a greater activity than a Class II peptide.

Specifically, to identify an immunomodulatory agent, two components are used. The first component is a Class II protein/peptide. The second component is a PCNA protein/peptide.

The MHC Class II protein/peptide used in the present method can either be an entire MHC Class II protein, a fragment of the Class II peptide that binds the PCNA protein, a protein that contains the Class II amino acid sequence, such as a fusion protein containing the Class II sequence or a recombinant host cell that expresses any of the Class II containing peptides. The preferred Class II peptide will contain from about residue 65 to about 79 of an MHC Class II protein. Most preferably, the peptide used will contain the amino acid sequence, NIAVLKHNLNIVIKR (Sequence ID NO: 1). In the examples that follow, a synthetic peptide corresponding to the Class II peptide is used. Additionally, the Class II containing peptide can contain more than one copy of the Class II sequence, such as in a palidromic or tandem repeat.

As an alternative to compounds containing the Class II peptide, agents that are identified in the present method that bind to the Class II binding site on the PCNA protein can be substituted for the Class II peptide. For example, an agent that is found to block Class II peptide/PCNA binding by binding to the Class II binding site on PCNA can be used in place of the Class II peptide for screening further compounds. For the sake of convenience, all of these agents will be collectively referred to as the Class II peptide.

The Class II peptide used in the present assay is preferably a human Class II peptide. The preferred Class II peptides used in the present method will be derived from an allelle selected from, but not limited to, HLA DP 0101, DQ 03011 and DR 0101. The most preferred Class II peptide will contain the sequence NIAVLKHNLNIVIKR SEQ ID No:1. A skilled artisan can readily use any Class II protein/fragment/expressing cell in the present method so long as it contains from about residue 65 to about residue 79 of an MHC Class II protein and it can bind to PCNA.

The PCNA peptide used in the present method can be any isolated member of the PCNA family of proteins so long as the member binds to a Class II peptide. The PCNA family member can be used in its entirety or a fragment of the PCNA protein or a fusion protein that contains the Class II binding site can be used. Alternatively, a cell expressing the PCNA, PCNA fragment, or fusion protein can be used. For the sake of convenience, all of these agents will be collectively referred to as the PCNA peptide.

The PCNA peptide used in the present assay is preferably a human PCNA peptide. The preferred PCNA peptide has the amino acid sequence disclosed by Kritina (et al, Cell 79:1233–1243 (1994). A skilled artisan can readily use any PCNA protein/fragment/expressing cell in the present method so long as it contains the Class II peptide binding site which is located from about residue 178 to about 261 on a human PCNA protein.

The source of the two peptide components will depend, primarily, on the nature of the peptides used. For example, synthetic chemistry can be used to produce peptides containing the specific contact site. Alternatively, the peptides can be isolated from a recombinant host.

To perform an assay according to the present invention, the Class II peptide and the PCNA peptide are incubated together in the presence and absence of an agent to be tested. The condition chosen will be based on the nature of the peptides used and the detection method employed. A skilled artisan can readily determine the appropriate conditions for any Class II/PCNA peptide pair.

After mixing under conditions that allow the association of the Class II peptide with the PCNA peptide, the mixture is analyzed to determine if the amount of binding of the Class II peptide to the PCNA peptide is decreased due to the presence of the test agent. Agents that block or decrease the binding of the Class II peptide with the PCNA peptide will be identified as decreasing the amount of binding present in a sample containing the agent.

As used herein, an agent is said to block or decrease Class II peptide/PCNA binding when the presence of the agent prevents or reduces the amount of association of the PCNA peptide with the Class II peptide. One class of agents will reduce or block the association by binding to the PCNA peptide while another class of agents will reduce or block the association by binding to the Class II peptide. The preferred agents of the present invention will bind to the PCNA peptide.

The Class II and PCNA peptides/proteins used in the present invention can be used in a variety of forms. The peptides can be used in a highly purified form, free from naturally occurring contaminants. Alternatively, a crude preparation containing a mixture of cellular components as well as the Class II and PCNA peptides can be used. So long as the association of the PCNA peptide with the agent to be tested and/or the Class II peptide can be identified in the sample, the Class II and PCNA peptides are in a suitable form for use in the the present assay.

To further aid in their use, the Class II and PCNA peptides may additionally be modified to contain a detectable label or signal generation system to facilitate detection. Methods for attaching agents such as fluorescence tags and secondary labeling agents, such as biotin, are well known in the art.

Further, the Class II and PCNA peptides may be attached to a solid support or matrix. For example, one or both peptides may be coupled to a substrate, such as the bottom of a multiwell microtiter plate, nitrocellulose or a newly developed biochip based substrate. Attaching one or both of the peptide components to a solid support allows the assay of the present invention to be used in high through put screening methods.

A variety of art known methods can be adapted and employed to detect whether an agent blocks or reduces the interaction of the Class II peptide with the PCNA peptide. Such methods include, but are not limited to, assays that employ a solid support, assays in solution phase, assays performed in a gel-type media, and assays that use a combination of these environments. An example of an assay would be one in which one or more of the Class II or PCNA peptides are immobilized on a solid support and is incubated in a solution with the agent to be tested and the other peptide of the Class II/PCNA pair. A secondary detection means, such as an antibody, is then used to determine the amount of the second peptide that binds to the immobilized peptide. Alternatively, the second peptide of the Class II/PCNA pair can be detectably labeled and its binding to the immobilized first peptide directly assessed. One format that is suitable for a solid phase based assay is immobilization of one of the members in a 96-well micro-titer plate. Such titer plates provide an efficient assay format for rapidly processing multiple samples in a high through put screening method.

Alternatively, both peptides of the Class II/PCNA pair can be in solution. After mixing, the binding of the Class II to the PCNA peptide can be detected using a variety of methods, for example detecting mobility shifts using electrophoretic means. One skilled in the art can readily appreciate how numerous assay-type/formats that are known in the art for use in competitive assays can be modified to use the Class II/PCNA peptide pair.

Direct binding to the Class II peptide or the PCNA peptide can be used as a first step in identifying agents that block Class II/PCNA peptide interaction. For example, in such methods, agents are first screened for the ability to bind to either the PCNA or Class II peptides. Agents that bind either the PCNA peptide or the Class II peptide are then screened for the ability to block Class II/PCNA peptide interaction, or for the ability to modulate a function of the immune system.

Agents that are assayed in the present methods can be randomly selected or rationally selected or designed. As used herein, an agent is said to be randomly selected when the agent is chosen randomly without considering the specific sequences involved in the association of the Class II peptide with the PCNA peptide. An example of randomly selected agents is the use of a chemical library or a peptide combinatorial library.

As used herein, an agent is said to be rationally selected or designed when the agent is chosen on a nonrandom basis that takes into account the sequence of the target site and/or its conformation in connection with the agent's action. There are two sites of actions for agents that block Class II peptide/PCNA peptide interactions: the PCNA peptide binding site on the Class II peptide and the Class II binding site on the PCNA peptide. The preferred agent for use in blocking an immune response will bind to the Class II binding site on the PCNA peptide. Agents can be rationally selected or rationally designed by utilizing the peptide sequences that make up the contact sites of the Class II/PCNA peptide pair. For example, a rationally selected peptide agent can be an agent that has a structure that mimics the PCNA binding site on the Class II peptide. Such agents will reduce or block the association of a Class II peptide with the PCNA peptide by binding to the PCNA peptide.

The agents of the present invention can be peptides, including peptides containing modified amino acids, vitamin derivatives, small molecules and carbohydrates. A skilled artisan can readily recognize that there is no limit as to the structural nature of the agents tested in the present assay methods.

One class of agents that block PCNA/Class II peptide binding are antibodies immunoreactive with critical positions of the Class II peptide or with the PCNA peptide. Antibody agents are obtained by immunization of suitable mammalian subjects with peptides, containing as antigenic regions, those portions of the Class II peptide or PCNA that are intended to be targeted by the antibodies. Critical regions include, but are not limited to, the contact sites involved in the association of the Class II peptide with the PCNA protein and sites that provide steric interference with the Class II contact site on the PCNA protein.

Antibody agents are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at the amino or carboxy terminus with a Cys residue or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. (See Harlow: Antibodies Cold Spring Harbor Press NY 1989) The immortalized cell lines secreting the desired antibodies are screened by immunoassay in which the antigen is the peptide hapten or is the PCNA or Class II peptide. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras with multiple species origin, or CDR grafted antibodies.

The antibodies thus produced are useful not only modulators of immune function, but are also useful in immunoassays.

C. Uses for agents that block the association of a Class II peptide with a PCNA peptide As provided in the Background section, Class II peptides have been shown to modulate a variety of biological responses, particularly those involving the immune system. In particular, Class II peptides have been shown to be potent inhibitors of CTL differentiation, proliferation and CTL mediated killing and has found use in increasing allograft tolerance and reducing the severity of autoimmune disorders such as rheumatoid arthritis. Therefore, one use of agents that block or reduce Class II/PCNA peptide binding is to modulate immune system responsiveness in the same fashion as the Class II peptides.

Specifically, immune system activity, such as CTL proliferation, differentiation and CTL mediated lysis, can be modulated by administering to a subject an agent that can block the interaction of the Class II peptide with a PCNA peptide, particularly by binding to the PCNA peptide.

As used herein, a subject can be any mammal, so long as the mammal is in need of modulation of immune activity. The term "mammal" is meant an individual belonging to the class Mammalia. The invention is particularly useful in the treatment of human subjects.

As used herein, immune system activity refers to the wide variety of cellular events in which cells of the immune system participate. In general, the Class II peptide has been shown to selectively inhibit events mediated by CTLs, and in particular CTL proliferation, differentiation and CTL mediated killing. Examples of situations where it is desirable to modulate such activity include, but are not limited to, transplant surgery and in the treatment of autoimnmune disorders. In each of these situations, it is desirable to selectively reduce CTL responsiveness.

As used herein, an agent is said to modulate an immune system activity, or reduce the severity of a pathological condition mediated by the immune system, when the agent prevents the normal immune activity of the subject. For example, an agent is said to modulate graft rejection when the agent reduces the rate of onset of graft rejection or reduces the severity of graft rejection.

D. Administration of Agents that modulate immune system activity

The agents of the present invention can be provided alone, or in combination with another agent that modulates a function of the immune system. For example, an agent of the present invention used to that reduce graft rejection can be administered in combination with other immunosuppressive agents. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents of the identified using the present screening methods. A composition comprising an agent identified using the present assay may also contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

E. Methods for targeting the pharmaceutical agents of the present invention

The present invention further provides methods for increasing the affinity of the agents of the present invention, as well as any other agents that blocks or reduces Class II peptide/PCNA interaction. Specifically the affinity of an agent that blocks the Class II peptide/PCNA interaction can be increased by covalently linking the agent to a second agent that has an equal or higher affinity for either PCNA or a Class II peptide. Such a second agent will preferably bind to another site on either the Class II protein or PCNA protein and will bring the Class II/PCNA blocking agent into close proximity to the target site. Such second agents can be, but are not limited to, antibody and peptide agents. The second agent can be covalently attached to the Class II/PCNA blocking agent using art know methods. Methods that employ linkers are particularly well suited for this use.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLE I

Isolation and Characterization of the Class II Binding Partner

Methods And Materials

Plasmid Construction: Synthetic oligonucleotides encoding the peptide DQ65-79 were designed using the most frequent codon for each amino acid. The sense and antisense oligonucleotides, which have BamHI and EcoRI at each end, were annealed and subcloned into pAs-1 vector (a high-copy-number yeast expression vector). The pXL-17 was created as the bait plasmid in the yeast two hybrid screen. In pXL-17, the peptide DQ65-79 was fused to the carboxyl terminal end of the yeast GAL4 DNA binding domain (GAL4-BD).

Yeast Two-Hybrid Screen: The primary screen was as follows: Yeast strain Y153 or Y190 were cotransformed by LiOAC method of Scheistl and Gietz (1989) with pXL-17 and human B cell cDNA library (gift from S. Elledge, Baylor College of Medicine, Texas) using salmon sperm DNA as carrier. The transformation mix was then plated on SC-medium, lacking tryptophan, leucine, and histidine, but including 50 mM 3-AT (Sigma). Plates were incubated at 30° C. for 4–6 days. The secondary screen was carried out by screening HIS+ colonies for beta-galactosidase activity using a filter-lift assay (Breeden and Nasmyth, 1985). Colonies were transferred onto Whattman 3 MM paper and permeabilized by liquid nitrogen freeze-thaw method. Filters were then overlayed on Whattman 3 MM paper saturated with Z-buffer-X-gal solution and incubated at 37° C. The time required for color development ranged from 30 minutes to overnight.

Recovery Of Library Plasmids From Yeast Cells: Library plasmids were rescued from yeast cells as described previously (Robzyk and Kassir, 1992) and used to transform DH5alpha via electroporation using a BRL electroporator according to the manufacturer's protocol. Transformants were plated on LB-ampicillin (10 μg/ml) plates.

Reconstitution Of Positive Yeast Two-Hybrid Interaction And Specificity Test: Library plasmids, recovered from positive yeast clones and amplified in E.coli, were co-transformed with pXL-17 bait plasmid into either Y153 or Y190 strain. Only those clones enabling transformants passing through both primary His selection and secondary LacZ screen were pursued further. Then the library plasmids were cotransformed with the following different bait plasmids: (1) pAS1-IGD (GAL4-DB-Bax protein fusion,); (2) pAS1-CDK2 (GAL4-DB-CDK2 protein fusion); and (3) pAS1-Lamin (GAL4-DB-Lamin protein fusion). (Plasmid 1 was a gift from L. Naumovski, Stanford University, California. Plasmids 2 and 3 were from S. Elledge, Baylor College of Medicine, Texas). Patches of cells were made from these transformants and beta-galactosidase colony lifting assay was performed as described previously.

Sequence Reaction And Analysis: Positive library plasmids were sequenced using dideoxy NTPs and Sequenase 2.0 (U.S. Biochemical). Sequence analysis and homology searches were performed using GCG and NCBI softwares.

In Vitro Binding Assay: The in vitro binding of peptides and proteins were performed as follows: PVDF membrane was precut into small dots. Dot membranes were briefly wetted with methanol and then rinsed with TBS buffer (10 mM Tris pH7.4, 150 mM Nacl). Synthetic peptides were spotted on to the center of the dot membrane with a gel-loading tip and incubated at room temperature for 10 minutes. The dots were wetted again briefly with methanol and rinsed with TBS buffer. These dot blots were blocked in 5% milk-TBST (0.1% Tween 20) for 1 hour, washed in TBS buffer, and incubated with 100 ng protein samples in TBS buffer containing 1% BSA (Sigma A-7888) and 0.1% Tween at 4° C. overnight. HSP70 protein was made recombinantly (gift from D. Hanson, Krensky's Lab, Stanford University, California). Native human PCNA was purified from Hela cells (gift from J. Hurwitz, Memorial Sloan Kettering Cancer Institute, New York). Dot blots were washed in TBST and incubated with the following different primary antibodies: monoclonal anti-PCNA antibody, p10, 1:1000 dilution, Santa Cruz Biotechnology, Inc.; monoclonal anti-HSP70 antibody, BRM22, 1:200 dilution, sigma; monoclonal anti-Histidine antibody, Clontech, Inc. After washing in TBST, the dot blots were incubated with horseradish peroxidase conjugated rabbit anti-mouse antibody (Dako) at 1:1000 dilution in TBST. Proteins were visualised by the enhanced chemiluminescence (ECL) reaction using hyperfilm-MP (Amersham).

Results

Isolation Of PCNA As A Binding Ligand For DQ65-79 Peptide: The general scheme of screening of peptide DQ binding proteins is outlined in FIG. 1. The primary screen is for the HIS marker and the secondary screen is for LacZ reporter activity. A positive yeast two hybrid interaction should enable the transcription of both His and LacZ genes. Analysis of 5×10 Exp(6) Trp+Leu+ transformants generated 28 His+LacZ+ positives, with one positive clone expressing a 600 base pair partial cDNA encoding amino acid (179-261) of the human proliferating cell nuclear antigen (PCNA).

Figure 2:
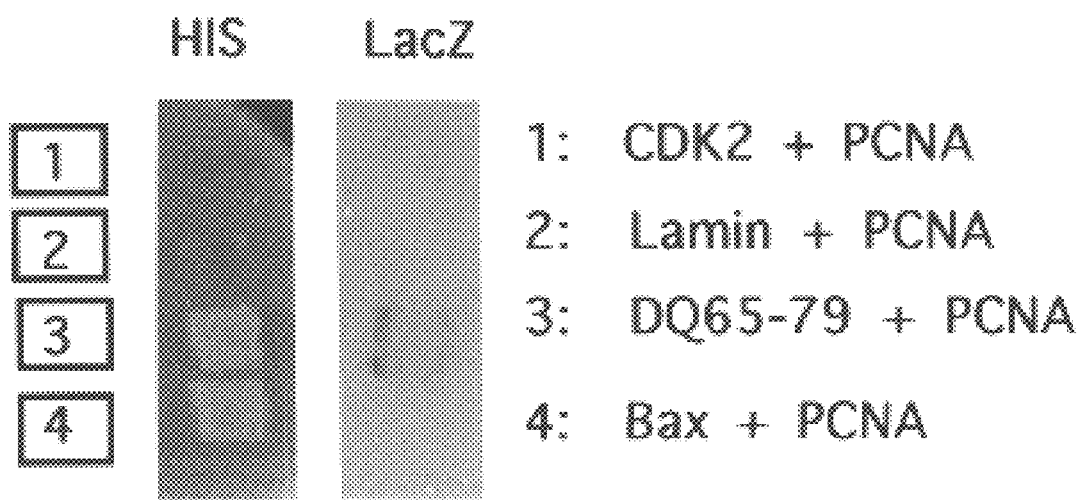
FIG. 2: DQ65-79 peptide interacts specifically with human PCNA in yeast. Different bait plasmids were cotransformed with the human PCNA clone which was found from the library screen. The left panel shows the patches of yeast cells on histidine deficiency plates with 50 mM 3AT. Cells on these patches were from single colony of the yeast transformants. The right panel shows the beta-galactosidase colony-lifting assay of the cell patches on left panel.

DQ65-79 Peptide Interacts Specifically With PCNA In Yeast: A yeast two-hybrid assay was used to assess the specificity of the interaction between DQ65-79 and PCNA in vivo. As shown in FIG. 2, the indicated GAL4 DNA binding domain (GAL4 DB) constructs and GAL4 activation domain PCNA constructs were used to cotransform a yeast strain possessing an integrated His marker and LacZ gene regulated by GAL4 protein binding sites. GAL4-DB-CDK2, —Lamin proteins are unable to activate His marker transcription to allow cellular growth on Histidine deficiency plates. Although GAL4-DB-Bax can somehow enable cellular growth, it cannot acitivate LacZ reporter activity. In contrast, GAL4-DB-DQ65-79 together with GAL4-AD-PCNA (179-261) not only allowed rapid cellular growth on histidine deficiency plates, but also enabled LacZ expression to allow color change in the beta-galactosidase assay. These data demonstrate that the DQ-PCNA interaction is specific in yeast.

Figure 3A:
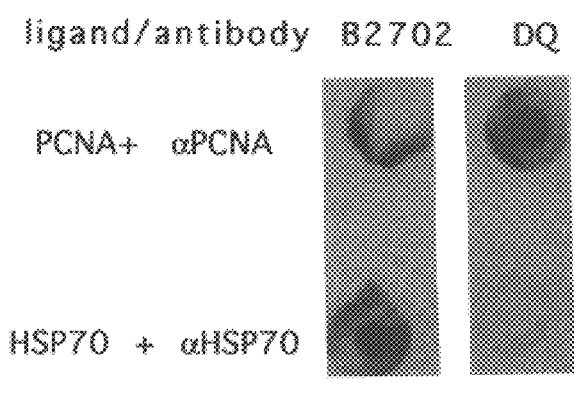
FIG. 3: DQ65-79 peptide binds native human PCNA protein in vitro. The DQ peptide was has been tagged with six histidines at the amino terminus in order to visualize the input amount.
Figure 3B:
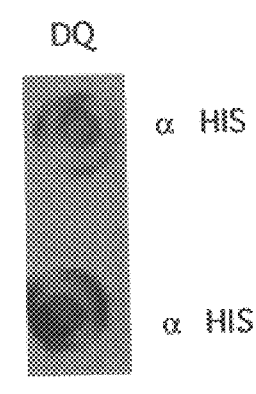

DQ65-79 Peptide Binds Native Human PCNA In Vitro: As shown in FIG. 3, native human PCNA (panel 2) can interact with DQ peptide but cannot bind recombinant HSP70 protein. As previously described, another immunosuppressant peptide (HLA-B2702.84-75,75-84 inverted repeat) did interact with recombinant HSP70 protein. Here we find HLA-B2702.84-75,75-84 peptide does bind human PCNA. These in vitro binding studies verify the interaction between PCNA and DQ65-79 identified in yeast in vivo. The DQ65-79 peptide used in this study was tagged with six histidines at the amino terminus in order to visualize the input of the amount of peptide in the assay. The histidine tagged DQ and the native DQ peptide behave the same in inhibition of CTL function and blocking T lymphocyte proliferation (data not shown).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

1         5               10              15 what is claimed is:

1. A method for identifying lymphocyte immunomodulating agents that block T-cell proliferation, said method comprising the steps of:

a) mixing
    i) a PCNA peptide or a cell selected from the group consisting of an isolated PCNA protein, a cell expressing a PCNA protein, a peptide comprising a fragment of a PCNA protein comprising an MHC Class II α chain peptide binding site, or a cell expressing a peptide comprising a fragment of a PCNA protein comprising an MHC Class II α chain peptide binding site, and
    ii) an MHC Class II α chain peptide or a cell selected from the group consisting of an isolated MHC class II protein, a cell expressing an MHC Class II α chain protein, a peptide comprising from about residue 65 to about residue 79 of an MHC Class II α chain protein, or a cell expressing a peptide comprising from about residue 65 to about residue 79 of an MHC Class II α chain protein, wherein said MHC Class II α chain protein or peptide binds to PCNA peptide; in the presence and absence of a candidate agent;

b) determining whether the presence of the candidate agent blocks or reduces the binding of the PCNA peptide to the Class II α chain peptide;

c) identifying immunomodulating agents that block T-cell proliferation as agents that block or reduce the binding of the Class II α chain peptide to PCNA peptide.

2. The method of claim 1, wherein said MHC Class II peptide comprises a peptide comprising from about residue 65 to about residue 79 of an MHC class II α chain protein selected from the group consisting of HLA DP 0101, DQ 03011 and DR 0101.

3. The method of claim 2, wherein said MHC Class II peptide comprises a peptide comprising the amino acid sequence depicted in SEQ ID No: 1.

4. The method of claim 1, wherein said PCNA peptide is a human PCNA peptide.

5. The method of claim 1 wherein said PCNA peptide comprises a peptide fragment of a member of the PCNA family of proteins that binds to the Class II peptide.

6. The method of claim 1, wherein one or both of said peptides that comprise the Class II sequence and the PCNA sequence is expressed on the surface of a cell.

7. The method of claim 1, wherein one or both of said peptides that comprise the Class II sequence or the PCNA sequence is provided as a fusion protein.

8. The method of claim 1, wherein one or both of said peptides that comprise the Class II sequence or the PCNA sequence is detectably labeled.

9. The method of claim 1, wherein one or both of said peptides that comprise the Class II sequence or the PCNA sequence is immobilized on a solid support.

10. The method of claim 1 wherein said agent is first tested for the ability to bind to a member of the PCNA family of proteins.

* * * * *